US012013307B2

(12) United States Patent
Maruyama et al.

(10) Patent No.: US 12,013,307 B2
(45) Date of Patent: Jun. 18, 2024

(54) METHOD FOR DIAGNOSING ROLLING DEVICE

(71) Applicant: NSK LTD., Tokyo (JP)

(72) Inventors: Taisuke Maruyama, Fujisawa (JP); Masayuki Maeda, Fujisawa (JP); Ken Nakano, Yokohama (JP)

(73) Assignee: NSK LTD., Tokyo (JP)

( * ) Notice: Subject to any disclaimer, the term of this patent is extended or adjusted under 35 U.S.C. 154(b) by 421 days.

(21) Appl. No.: 17/422,888

(22) PCT Filed: Jan. 10, 2020

(86) PCT No.: PCT/JP2020/000681
§ 371 (c)(1),
(2) Date: Jul. 14, 2021

(87) PCT Pub. No.: WO2020/149233
PCT Pub. Date: Jul. 23, 2020

(65) Prior Publication Data
US 2022/0074813 A1    Mar. 10, 2022

(30) Foreign Application Priority Data

Jan. 15, 2019   (JP) ................. 2019-003990

(51) Int. Cl.
*G01M 13/04*   (2019.01)
*F16C 19/06*   (2006.01)
(Continued)

(52) U.S. Cl.
CPC ............. *G01M 13/04* (2013.01); *F16C 19/06* (2013.01); *F16C 19/522* (2013.01);
(Continued)

(58) Field of Classification Search
CPC ....... G01M 13/04; F16C 19/06; F16C 19/522; F16C 19/546; F16C 33/66; F16C 2233/00;
(Continued)

(56) References Cited

U.S. PATENT DOCUMENTS 10,429,373 B2 * 10/2019  Maeda ................. G01M 13/04
2009/0315574 A1  12/2009  Akiyama et al.
(Continued)

FOREIGN PATENT DOCUMENTS

EP    1980840 A1   10/2008
EP    2505999 A1   10/2012
(Continued)

OTHER PUBLICATIONS

International Search Report (PCT/ISA/210) issued by the International Searching Authority in International Application No. PCT/JP2020/000681, dated Feb. 10, 2020.
(Continued)

*Primary Examiner* — Freddie Kirkland, III
(74) *Attorney, Agent, or Firm* — Sughrue Mion, PLLC

(57) ABSTRACT

A method for diagnosing a rolling device (10) including an outer member (1), an inner member (3), and rolling elements (5) includes: applying an AC voltage to an electric circuit including the outer member (1), the rolling elements (5), and the inner member (3); measuring an impedance and a phase angle of the electric circuit when the AC voltage is applied; and measuring a dielectric constant of a lubricant at least one of between the outer member (1) and the rolling elements (5) and between the inner member (3) and the rolling elements (5) based on the measured impedance and the measured phase angle.

7 Claims, 8 Drawing Sheets

(51) Int. Cl.
  *F16C 19/52* (2006.01)
  *F16C 19/54* (2006.01)
  *F16C 33/66* (2006.01)
  *G01N 27/22* (2006.01)
(52) U.S. Cl.
  CPC ............ *F16C 19/546* (2013.01); *F16C 33/66* (2013.01); *G01N 27/221* (2013.01); *F16C 2233/00* (2013.01); *F16C 2237/00* (2013.01)
(58) Field of Classification Search
  CPC .. F16C 2237/00; F16C 19/52; F16C 33/6688; G01N 27/221; G01N 33/2888
  See application file for complete search history.

(56) References Cited

U.S. PATENT DOCUMENTS

| | | | |
|---|---|---|---|
| 2009/0320567 | A1 | 12/2009 | Takahashi et al. |
| 2010/0157304 | A1 | 6/2010 | Takahashi et al. |
| 2012/0229151 | A1 | 9/2012 | Katafuchi |
| 2017/0248572 | A1* | 8/2017 | Byington ............ G01N 33/2888 |
| 2019/0128866 | A1 | 5/2019 | Maeda et al. |

FOREIGN PATENT DOCUMENTS

| | | |
|---|---|---|
| JP | 49-042496 B1 | 11/1974 |
| JP | 11-152490 A | 6/1999 |
| JP | 2007-310611 A | 11/2007 |
| JP | 4942496 B2 | 5/2012 |
| WO | 2007/083520 A1 | 7/2007 |
| WO | 2011/065340 A1 | 6/2011 |
| WO | 2018/128062 A1 | 7/2018 |

OTHER PUBLICATIONS

Written Opinion (PCT/ISA/237) issued by the International Searching Authority in International Application No. PCT/JP2020/000681, dated Feb. 10, 2020.
Office Action dated Mar. 11, 2022 by the Intellectual Property Office of India in counterpart Indian Patent Application No. 202117031372.
Communication dated Feb. 16, 2022 by the European Patent Office in European Patent Application No. 20741216.4.
Office Action dated Apr. 19, 2022, issued by the Japan Patent Office in counterpart Japanese Patent Application No. 2020-566401.

\* cited by examiner

METHOD FOR DIAGNOSING ROLLING DEVICE

TECHNICAL FIELD

The present invention relates to a method for diagnosing a rolling device.

BACKGROUND ART

A rolling device such as a bearing is used in a wide variety of industrial fields such as automobiles and various industrial machines. Grasp of a lubrication state inside the rolling device is an extremely important matter from the viewpoint of securing smooth operation of the machine, life of the rolling device, and the like. By appropriately grasping the lubrication state, it is possible to perform maintenance such as supply of various lubricants (oil, grease, and the like) and replacement of the rolling device at an optimum timing without excess or deficiency. However, since it is difficult to directly perform visual observation of the lubrication state, a method of monitoring vibration, sound, and oil film state is proposed as a diagnosis method for a rolling device.

In Patent Literature 1, an AC voltage is applied to a rotating wheel of a rolling device in a non-contact state, and an oil film state of a bearing can be estimated using a measured electrostatic capacity. That is, an electrical equivalent circuit is modeled regarding the oil film as a capacitor, an AC voltage is applied to the rotating wheel of the rolling device in a non-contact state, and the electrostatic capacity of the oil film is measured. Since the electrostatic capacity and an oil film thickness (lubricating film thickness) have a correlation, the state of the oil film is estimated from this correlation.

CITATION LIST

Patent Literature

Patent Literature 1: Japanese Patent No. 4942496

SUMMARY OF INVENTION

Technical Problem

According to the technique disclosed in Patent Literature 1, it is possible to measure the oil film thickness. However, this method is capable of calculating only the oil film thickness, and is difficult to grasp other elements that affect the lubrication state.

The present invention provides a diagnosis method for a rolling device capable of grasping a lubrication state of a rolling device in consideration of not only a lubricating film thickness but also a metal contact ratio.

Solution to Problem

A method for diagnosing a rolling device including an outer member, an inner member, and a rolling element, and includes: applying an AC voltage to an electric circuit including the outer member, the rolling element, and the inner member; measuring an impedance and a phase angle of the electric circuit when the AC voltage is applied; measuring a dielectric constant of a lubricant at least one of between the outer member and the rolling element and between the inner member and the rolling element based on the measured impedance and the measured phase angle; and calculating a wear powder concentration of the lubricant from the measured dielectric constant.

Advantageous Effects of Invention

According to the present invention, it is possible to grasp not only a thickness of a lubricating film but also a metal contact ratio in a rolling device, and more specifically, it is possible to diagnose a lubrication state of the rolling device more accurately. In particular, in the present invention, since a wear amount of the rolling device is also calculated, it is possible to diagnose the lubrication state of the rolling device more accurately.

BRIEF DESCRIPTION OF DRAWINGS

FIG. 2A is an electric circuit corresponding to one ball test piece (rolling element) shown in FIG. 1, and FIG. 2B is an electric circuit of the entire rolling apparatus.

DESCRIPTION OF EMBODIMENTS

Hereinafter, an embodiment of a diagnosis method for a rolling apparatus (bearing apparatus) according to the present invention will be described in detail with reference to the drawings.

As an oil film diagnosis technique in a rolling apparatus or related art, there is an inspection device disclosed in Patent Literature 1. In a configuration of the inspection apparatus, modeling is performed regarding an oil film as a capacitor, an AC voltage is applied to a rotating wheel of a rolling apparatus in a non-contact state, and an electrostatic capacity of the oil film is measured. Since there is a specific correlation between the electrostatic capacity and an oil film thickness, it is possible to estimate an oil film state of the rolling apparatus. However, in the method of Patent Literature 1, only the oil film thickness is measured, and it is difficult to grasp a metal contact ratio. In addition, since an electrostatic capacity outside a Hertzian contact area is not considered, an estimation accuracy of the value of the oil film thickness itself is not high.

The present invention establishes a method (impedance method) capable of applying an AC voltage to an elastohydrodynamic (EHD) contact area, and measuring the oil film thickness and a rupture ratio of the oil film in the EHD contact area from a measured complex impedance Z. By using this method, the oil film thickness can be measured with high accuracy. Here, a process of deriving the oil film thickness and the rupture ratio (metal contact ratio) of the oil film will be described.

Figure 1:
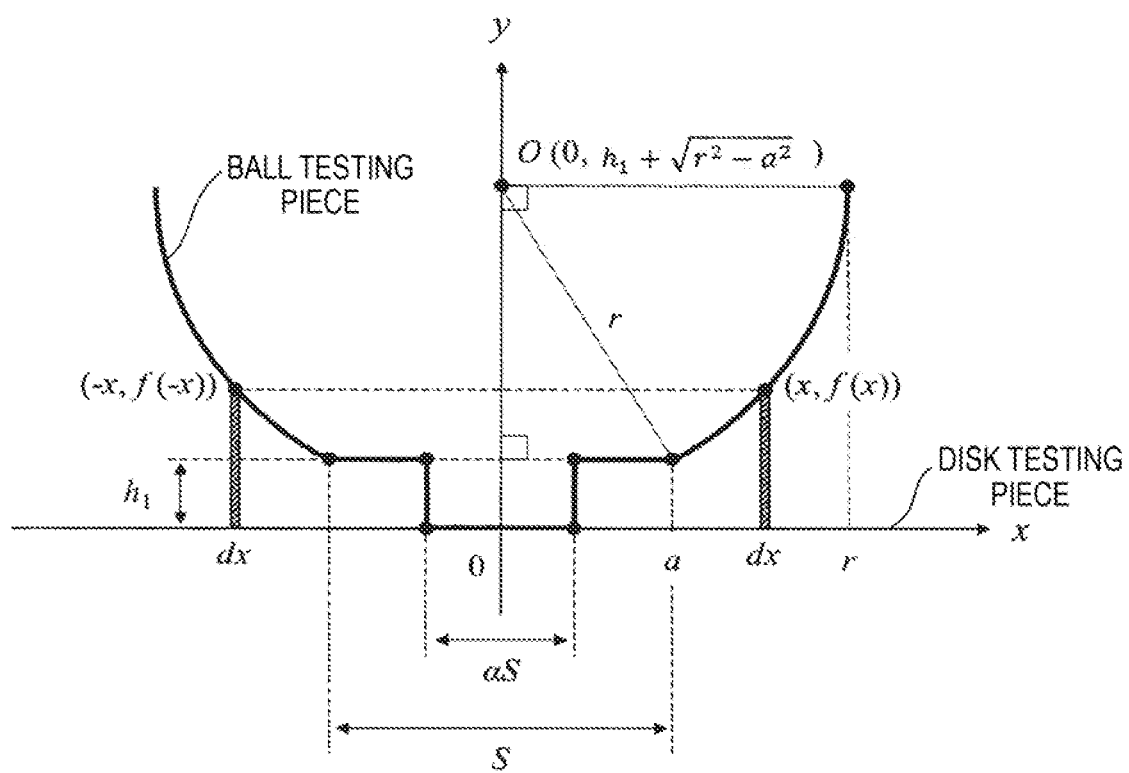
FIG. 1 is a graph illustrating a physical model under a mixed lubrication condition when a ball test piece is pressed against a disk test piece.

FIG. 1 is a graph illustrating a physical model under a mixed lubrication condition when a ball test piece is pressed against a disk test piece. In this model, the disk test piece corresponds to an outer ring or an inner ring of a rolling apparatus, and the ball test piece corresponds to a rolling element of a rolling apparatus. A y axis represents an axis in an oil film thickness direction, and an x axis represents an axis in a direction orthogonal to the oil film thickness direction. In addition, h1 is an oil film thickness at a portion where an oil film is formed in the EHD contact area, a is a Hertzian contact circle radius, r is a radius of the ball test piece, S is a Hertzian contact area, and α is a rupture ratio of the oil film. Therefore, an area where the oil film is ruptured in the EHD contact area is represented by αS as shown in FIG. 1. In addition, f(x) in FIG. 1 is a function representing a y coordinate of the surface of the ball test piece in a range of (a≤x≤r) other than the EHD contact area, and is expressed by the following Equation (1).

$$f(x) = h_1 + \sqrt{r^2 - a^2} - \sqrt{r^2 - x^2} \tag{1}$$

Since an actual ball test piece is elastically deformed when receiving a load, and strictly speaking, the ball test piece is not a sphere outside the EHD contact area, but is assumed as a sphere even after deformation as shown in Equation (1) in the present invention.

Normally, an area having a so-called horseshoe shape in which the oil film is thin exists in the EHD contact area, but an oil film thickness $h_a$ (average oil film thickness) that is an average in the EHD contact area was determined in the present invention. Therefore, in a case where the oil film is ruptured in a part of the EHD contact area, the average oil film thickness $h_a$ to be determined is expressed by the following Equation (2) using the rupture ratio α and the oil film thickness h1 of the oil film.

$$h_\alpha = (1-\alpha)h_1 \tag{2}$$

Figure 2A:
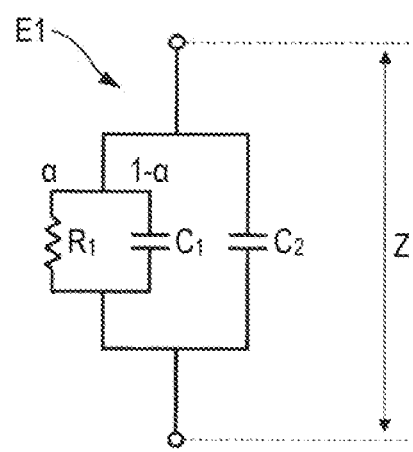
FIGS. 2A and 2B are diagrams of an electric circuit in diagnosis of a rolling apparatus, where

FIG. 2A is a diagram of an electric circuit (equivalent electric circuit) E1 obtained by converting a physical model of FIG. 1 into an electric circuit that is electrically equivalent. Here, $R_1$ is a resistance at an area where the oil film is ruptured, $C_1$ is an electrostatic capacity due to the oil film in the Hertzian contact area, and $C_2$ is an electrostatic capacity generated outside the Hertzian contact area when it is assumed that a space between two surfaces of the disk test piece and the ball test piece is filled with the lubricant (lubricating oil or grease) up to a position of x=r in FIG. 1. That is, in the present invention, an area outside the EHD contact area is also taken into consideration as a capacitor. The oil film in the Hertzian contact area forms a parallel circuit of the capacitor $C_1$ (electrostatic capacity $C_1$) and the resistance $R_1$ (resistance value $R_1$), and the parallel circuit and the capacitor $C_2$ (electrostatic capacity $C_2$) outside the Hertzian contact are connected in parallel.

Figure 2B:
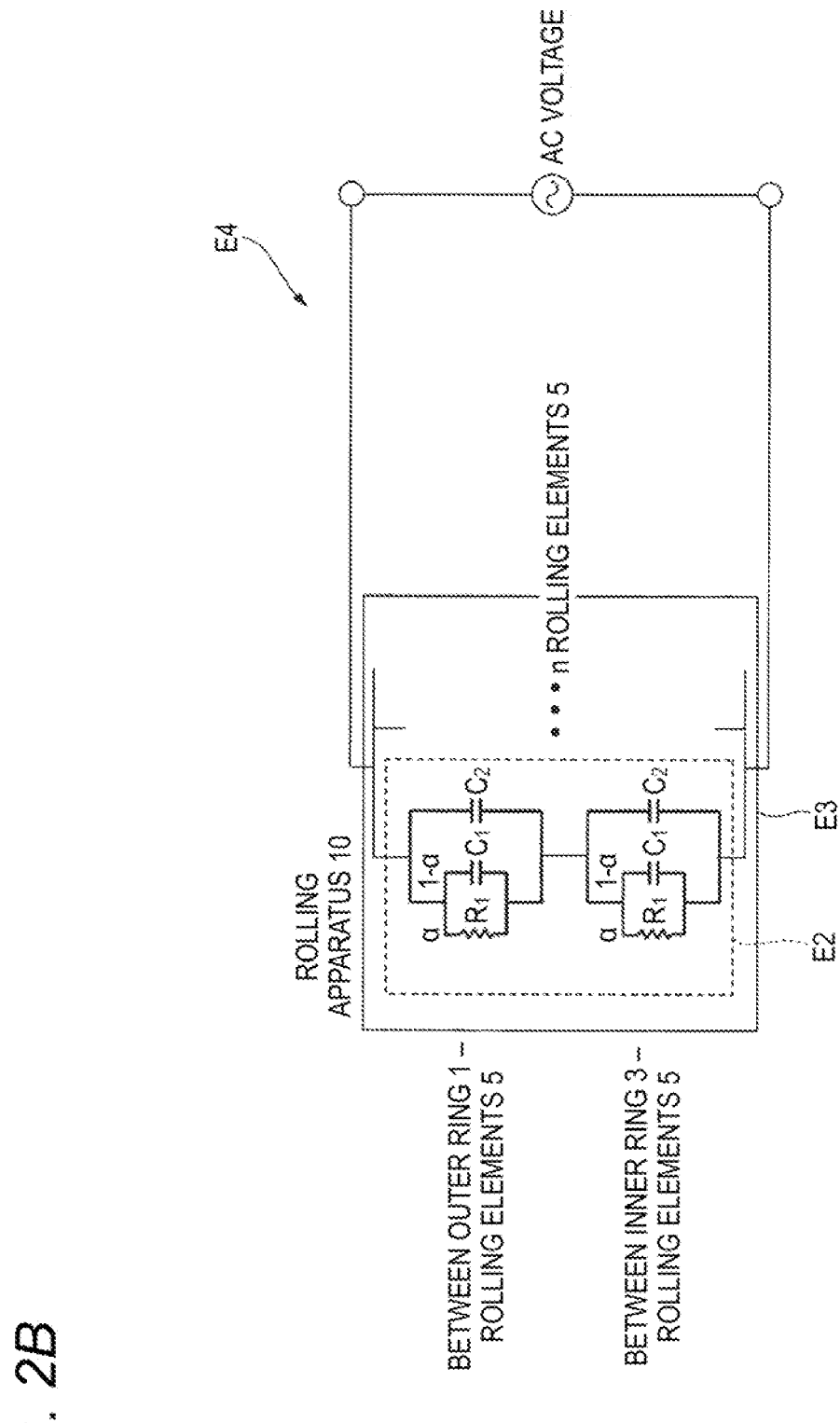

FIG. 2B shows an electric circuit E4 when the physical model of FIG. 1 is applied to a rolling apparatus 10 (see FIG. 4) having an outer ring 1 and an inner ring 3. Since each rolling element 5 is in contact with both the outer ring 1 and the inner ring 3, as shown in FIG. 2B, an electric circuit E2 in which two electric circuits E1 (between the outer ring 1 and the rolling element 5 and between the inner ring 3 and the rolling element 5) are connected in series is formed for each rolling element 5.

Further, when n rolling elements 5 are provided in the rolling apparatus 10, n electric circuit E2 are connected in parallel. Therefore, as shown in FIG. 2B, the rolling apparatus 10 including all the n rolling elements 5 forms an electric circuit E3. In diagnosis of the rolling apparatus 10 of the present embodiment, an AC voltage is applied between the outer ring 1 and the inner ring 3 of the rolling apparatus 10 from a power source, so that an entire electric circuit E4 shown in FIG. 2B is formed.

Here, the AC voltage V applied to the electric circuit in FIG. 2A is expressed by the following Equation (3), $$V = |V|\exp(j\omega t) \tag{3}$$

A current I flowing through the entire electric circuit in FIG. 2A is expressed by the following Equation (4).

$$I = |I|\exp(j\omega t) \tag{4}$$

Therefore, the complex impedance Z of the entire electric circuit in FIG. 2(a) is expressed by the following Equation (5).

$$Z = V/I = |V/I|\exp(j\theta) = |Z|\exp(j\theta) \tag{5}$$

Here, j is an imaginary number, t is a time, ω is an angular frequency of the voltage, and θ is a shift of a phase of the voltage and the current, that is, a phase angle. It can be seen from Equation (5) that the complex impedance Z includes two independent variables of an absolute value |Z| of the complex impedance Z and the phase angle θ. That means that two independent parameters (here, the average oil film thickness $h_a$ and the rupture ratio α) can be measured through measurement of the complex impedance Z.

Here, the complex impedance Z of the entire electric circuit shown in FIG. 2A is expressed by the following Equation (6).

$$Z^{-1} = R_1^{-1} + j\omega(C_1 + C_2) \tag{6}$$

Further, from the Equation (6), the following equations (7) and (8) can be obtained.

$$R_1 = |Z|/\cos\theta \tag{7}$$

$$\omega(C_1 + C_2) = -\sin\theta/|Z| \tag{8}$$

Here, the resistance $R_1$ of the region where the oil Film is ruptured in the Equation (7) is inversely proportional to the contact area, and thus is expressed by the following Equation (9).

$$R_1 = R_{10}/\alpha \tag{9}$$

Here, $R_{10}$ is a resistance in a stationary state (that is, α=1). $R_{10}$ is expressed by the following Equation (10) from Equation (6), where $|Z_0|$ is an impedance in a stationary state and $\theta_0$ is a phase angle.

$$R_{10} = |Z_0|/\cos\theta_{0\,tm} \tag{10}$$

Therefore, the rupture ratio α is expressed by the following Equation (11) from Equations (7), (9), and (10).

$$\alpha = |Z_0|\cos\theta/|Z|\cos\theta_0 \tag{11}$$

The electrostatic capacity $C_1$ due to the oil film in the Hertzian contact area is expressed by the following Equation (12) using a dielectric constant ε of the lubricant used for the test.

$$C_1 = \varepsilon(1-\alpha)S/h_1 = \varepsilon(1-\alpha)\pi a^2/h_1 \tag{12}$$

On the other hand, the electrostatic capacity $C_2$ generated outside the Hertzian contact area can be regarded as being formed by connecting annular capacitors each having a minute width dx, a length 2πx, and a height f(x) in parallel in a range of a≤x≤r as indicated by the shaded area in FIG. 1. Therefore, the electrostatic capacity $C_2$ is expressed by the following Equation (13).

[Equation 13]

$$C_2 = \varepsilon \int_a^r \frac{2\pi x}{f(x)} dx = 2\pi\varepsilon \left( (h_1 + \sqrt{r^2 - a^2}) \ln\left(\frac{h_1 + \sqrt{r^2-a^2}}{h_1}\right) - \sqrt{r^2-a^2} \right) \quad (13)$$

Here, since r>>a and r>>h1 are generally satisfied, the electrostatic capacity C2 can be approximated by the following Equation (14) based on Equation (13).

$$C_2 \approx 2\pi r \varepsilon (\ln(r/h_1) - 1) \quad (14)$$

From the above Equations (8), (12), and (14), the following Equation (15) is obtained.

[Equation 15]

$$\frac{r}{h_1} \exp\left(\frac{(1-\alpha)a^2}{2rh_1}\right) = \exp\left(1 - \frac{\sin\theta}{2\pi r w \varepsilon |Z|}\right) \quad (15)$$

Here, in order to obtain h1 in Equation (15), a Lambert W function is used. With respect to any complex number z, a Lambert W function W(z) is defined by the following Equation (16).

$$W(z)e^{W(z)} = z \quad (16)$$

Therefore, from the Equations (2), (15), and (16), the obtained average oil film thickness $h_a$ is expressed by the following Equation (17).

[Equation 17]

$$h_a = \frac{(1-\alpha^2)a^2}{2r} / W\left(\frac{(1-\alpha)a^2}{2r^2} \exp\left(1 - \frac{\sin\theta}{2\pi r \omega \varepsilon |Z|}\right)\right) \quad (17)$$

That is, from the Equations (11) and (17), the average oil film thickness $h_a$ and the oil film rupture ratio $\alpha$ can be calculated by measuring the impedance and the phase in the stationary state and at the time of forming the oil film.

The above description relates to the electric circuit E1 of FIG. 2A as a basic configuration, but can also be applied to the electric circuit E4 of FIG. 2B by taking the number of the rolling elements 5 of the rolling apparatus 10 into consideration. In the electric circuit E4, two contact points where one rolling element 5 is in contact with the outer ring 1 and the inner ring 3 correspond to a series circuit including two electric circuits E1, and the total number (n) of the rolling elements 5 in the rolling apparatus 10 corresponds to the number of parallel circuits each including two electric circuits E1 connected in series. Further, when a plurality of rolling apparatuses 10 are present (two in the example of FIG. 4 to be described later), electric circuits E3 of FIG. 2B are connected in parallel to the AC voltage.

Figure 3:
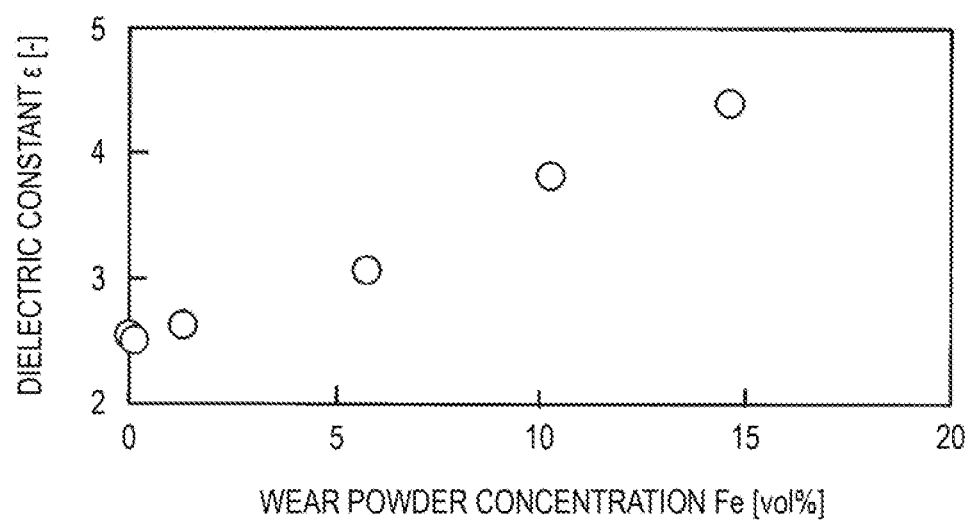
FIG. 3 is a graph illustrating a relationship between a wear powder concentration in a lubricant and a dielectric constant of the lubricant.

In a rolling apparatus, wear (mainly wear that occurs in the region of αS in FIG. 1) occurs to the members as the operating time elapses, and such wear is estimated to affect the performance and the lubrication state. In a case where wear occurs in the rolling apparatus, the average oil film thickness $h_a$ obtained by Equation (17) is generally larger than a theoretical oil film thickness he (Hamrock B J and Dowson D. Isothermal elastohydrodynamic lubrication of point contacts: part III-fully flooded results. ASME Trans J Lubricat Technol 1977; 99: 264-275.). This is because the dielectric constant ε of the lubricant is increased due to inclusion of wear powder in the oil. FIG. 3 is a graph showing a relationship between a wear powder concentration Fe in the lubricant and the dielectric constant ε of the lubricant. The dielectric constant ε of the lubricant increases as the wear powder concentration Fe increases. That is, a degree of wear (wear powder concentration and wear amount) can be monitored by calculating the dielectric constant assumed from the measured oil film thickness. Here, a process of calculating the dielectric constant will be described.

It is assumed that the oil film thickness h1 in the oil film formation portion within the EHD or elasto-hydrodynamic lubrication (EHL) contact area is expressed as follows using an oil film thickness $h_{limit}$ of the oil film and the rupture ratio α at which metal contact starts to occur. This is for the purpose of correcting a calculated oil film thickness thicker than a theoretical value to the same oil film thickness as the theoretical value. The oil film thickness $h_1$ in Equation (18) is basically the same concept as those in Equations (1) and (2), and $h_a = (1-\alpha)^2 h_{limit}$ can also be obtained from the Equations (2) and (18).

$$h_1 = (1-\alpha) h_{limit} \quad (18)$$

When a phase angle θ satisfying the above equation is θ', the rupture ratio α is expressed by the following Equation (19) using the absolute value |Z| of the measured complex impedance from Equation (11).

$$\alpha = |Z_0| \cos\theta' / |Z| \cos\theta_0 \quad (19)$$

From Equations (8), (12), and (14), the following Equation (20) is obtained.

$$2\pi\varepsilon\omega((1-\alpha)\alpha^2/2h_1 + r(\ln(r/h_1)-1)) = -\sin\theta'/|Z| \quad (20)$$

Here, the absolute value |Z| of the complex impedance Z is erased by Equation (20)/Equation (19), and the following Equation (21) is obtained.

[Equation 21]

$$\frac{2\pi\varepsilon\omega\left((1-\alpha)\alpha^2/2h_1 + r(\ln(r/h_1)-1)\right)}{\alpha} = -\frac{\cos\theta_0}{|Z_0|}\tan\theta' \quad (21)$$

By substituting Equation (18) into Equation (21), the following Equation (22) is obtained.

[Equation 22]

$$\theta' = -\tan^{-1}\left(\frac{2\pi\varepsilon\omega|Z_0|}{\alpha\cos\theta_0}\left(\frac{a^2}{2h_{limit}} + r\left(\ln\left(\frac{r}{(1-\alpha)h_{limit}}\right) - 1\right)\right)\right) \quad (22)$$

That is, the phase angle θ' satisfying Equation (18) can be calculated from the rupture ratio α of the oil film and the oil film thickness $h_{limit}$ at which the metal contact starts to occur. Therefore, an average oil film thickness $h_a'$ after correction in the EHL contact area assumed from the assumption of Equation (18) is expressed by the following Equation (23) using the absolute value |Z| of the complex impedance Z and the phase angle θ'.

[Equation 23]

$$h'_a = \frac{(1-\alpha^2)a^2}{2r} \bigg/ W\left(\frac{(1-\alpha)a^2}{2r^2}\exp\left(1 - \frac{\sin\theta'}{2\pi r\omega\varepsilon|Z|}\right)\right) \quad (23)$$

Further, the assumed dielectric constant ε' after wearing can be expressed by the following Equation (24) using the phase angle θ'.

[Equation 24]

$$h_a = \frac{(1-\alpha^2)a^2}{2r} \bigg/ W\left(\frac{(1-\alpha)a^2}{2r^2}\exp\left(1 - \frac{\sin\theta'}{2\pi r\omega\varepsilon'|Z|}\right)\right) \quad (24)$$

Therefore, the dielectric constant ε' is expressed by Equation (25) using the rupture ratio α, the average oil film thickness $h_a$, and the phase angle θ'.

[Equation 25]

$$\varepsilon' = \frac{\sin\theta'}{2\pi\omega|Z|\left((1-\alpha)^2 a^2/2h_a + r(\ln(r(1-\alpha)/h_a) - 1)\right)} \quad (25)$$

A right side of the dielectric constant ε' of the Equation (25) is all previously defined values and previously described values, so that the dielectric constant ε' can be calculated.

The point in the calculation method described above is to assume the oil film thickness h1 in the oil film forming portion by any method, and this assumption method is not particularly limited.

For example, instead of the oil film thickness $h_{limit}$ at which metal contact occurs in Formula (18), for example, a surface roughness (mean square roughness [nm]: Rq1, Rq2) prescribed in JISB0601 (2013) may be used. Therefore, h1 may be obtained by using the following Equation (18)' instead of Equation (18), so as to further calculate ε'. As a parameter for giving the degree of inter-projection interference in the EHL contact area, a film thickness ratio λ value is generally used (reference document: Tribology, Yamamoto Yuji, Kaneda Motohiro, Rikogakusha Publishing Co., Ltd., 2007). Here, λ value <3, that is, a phenomenon in which metal contact starts when at about three times the roughness is known, and such a phenomenon is used.

[Equation 26]

$$h_1 = (1-\alpha) \times 3\sqrt{R_{q1}^2 + R_{q2}^2} \quad (18)'$$

When the theoretical oil film thickness hc is known, h1 may be obtained by using the following Equation (18)" instead of Equation (18), so as to further calculate ε'.

$$h_1 = h_c/(1-\alpha) \quad (18)''$$

Examples of the present invention will be described below.

Figure 4:
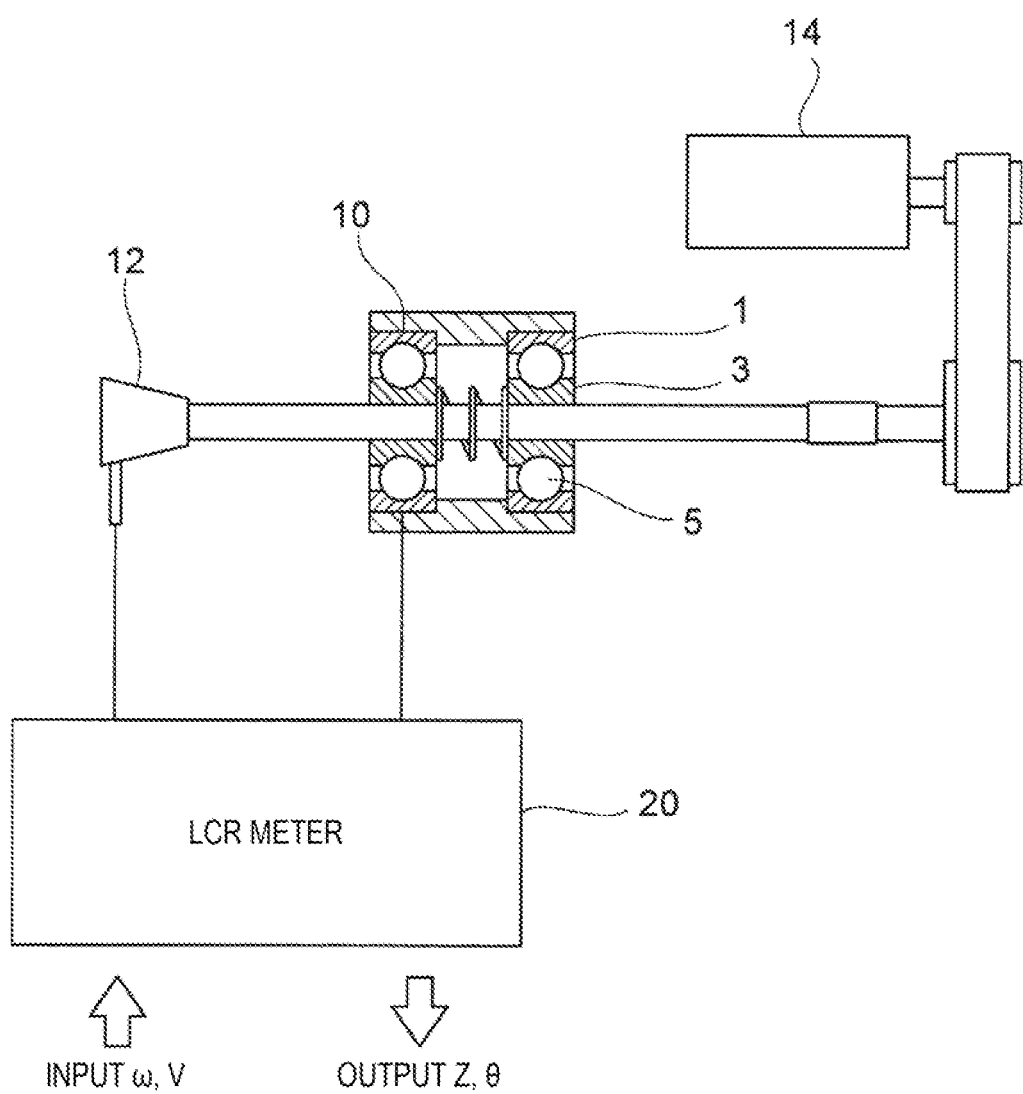
FIG. 4 is a conceptual diagram of a rolling apparatus and a testing device thereof.

FIG. 4 is a conceptual diagram of the rolling apparatus (bearing apparatus) 10 and a testing device for testing the rolling apparatus 10. The rolling apparatus 10 includes the fixed outer ring (outer member) 1, the inner ring (inner member) 3 which is a ring on a rotary side fitted to a rotating shaft 16, and a plurality of rolling elements 5 interposed between a raceway surface formed on an inner peripheral surface of the outer ring 1 and a raceway surface formed on an outer peripheral surface of the inner ring 3. An oil film (lubricating film) including the lubricant such as oil or grease supplied for lubrication exists between the outer ring 1 and the rolling elements 5 and between the inner ring 3 and the rolling elements 5. The rolling apparatus 10 is applied to a moving body such as an automobile, a two-wheeled vehicle, or a railway vehicle, an industrial machine, a machine tool, or the like, but the device to which the rolling apparatus 10 is applied is not particularly limited.

One end of a drive shaft penetrating the rolling apparatus 10 is connected to a general LCR meter 20 (also serving as the AC voltage) via a rotary connector 12, and the other end of the drive shaft is connected to a drive motor 14. The rotary connector 12 can be configured by attaching a carbon brush to a rotary ring at the one end of the drive shaft or by attaching a slip ring to the drive shaft, but is not particularly limited.

In the testing device of FIG. 4, a frequency ω of the AC voltage and a voltage V of the AC voltage are input to the LCR meter 20. In response to the input, the LCR meter 20 outputs the absolute value |Z| and the phase angle θ of the impedance of the rolling apparatus 10 connected to the LCR meter 20.

The lubricant used is a poly-α-olefin, and has a kinematic viscosity at 40° C. of 19 mm²/s and a dielectric constant of 2.1. Measurement conditions are as follows.
Temperature: 25° C.
Rotational speed of rotating shaft: 50 to 6000 rpm
Radial load: 0 N
Axial load: 30 N
Maximum contact pressure: 0.9 GPa First, the resistance (contact state resistance) $R_{10}$ (α=1) of the metal contact portion at the time of stop, that is, in a state where no oil film was present was measured (refer to Equation (10)). Thereafter, the impedance (absolute value) |Z| and the phase angle θ were measured while applying an alternating current.

Figure 5:
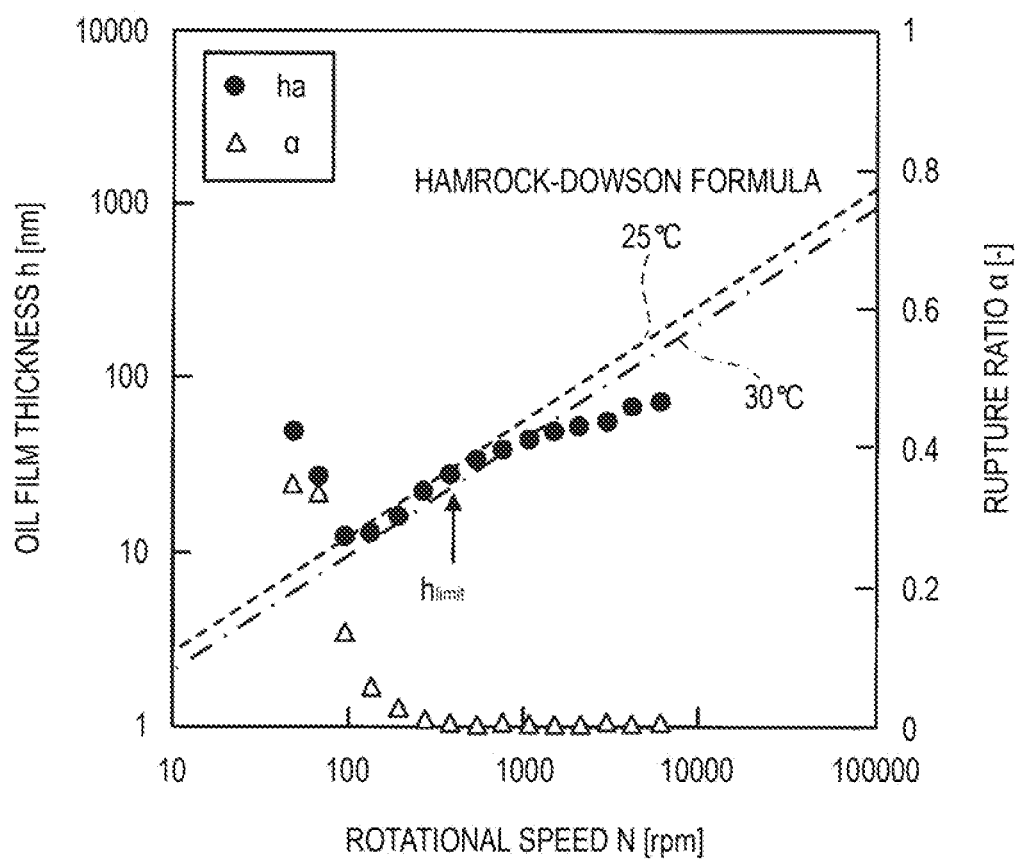
FIG. 5 is a graph of a result of measuring an average oil film thickness and a rupture ratio of oil film while changing a rotational speed of a rotating shaft.

Next, using Equations (11) and (17), the average oil film thickness $h_a$ and the rupture ratio α of the oil film were measured while changing the rotational speed N of the rotating shaft. FIG. 5 is a graph showing the measurement results.

From FIG. 5, it is understood that in a high rotation range where the rotation speed N is high, the oil film thickness $h_a$ is smaller than the theoretical oil film thickness $h_c$ obtained by a Hamrock-Dowson equation described in the paper related to the theoretical oil film thickness $h_c$ described above. In the graph of FIG. 5, the theoretical oil film thickness $h_c$ at room temperature (25° C.) at which the experiment was performed is indicated by a broken line. However, since an outer ring temperature was 33° C. at a rotational speed of 6000 rpm, the theoretical oil film thickness $h_c$ at 30° C., which can be estimated to represent a value close to the theoretical oil film thickness $h_c$ over the entire rotational speed, is also indicated by a dashed line. Since the actual oil film thickness is smaller than the theoretical oil film thickness in the high rotation region, this region is expected to be a depleted lubrication region (the lubricant is removed from a transfer surface between the rolling elements and the outer ring or the inner ring and thus is not sufficiently lubricated). Actually, in the high rotational speed range, as the rotational speed N increases, the rupture ratio α of the oil film decreases and the average oil film thickness $h_a$ increases, which are not contradictory.

On the other hand, in a low rotation speed range (<100 rpm) where the rotation speed N is low, as the rotation speed N increases, both the rupture ratio α and the oil film thickness $h_a$ of the oil film decrease, which are contradictory. In addition, a result was obtained that the oil film thickness $h_a$ was larger than the theoretical oil film thickness $h_c$.

Regarding this phenomenon which is apparently contradictory, the inventors examined and studied previous research, and focused on a phenomenon as shown in FIG. 3 that the dielectric constant of the lubricant increases as the wear powder concentration contained in the lubricant increases. That is, it is considered that since wear occurs in the contact area and the dielectric constant of the lubricant increases, the average oil film thickness $h_a$ obtained from the Equation (17) exhibits a behavior contrary to the rupture ratio α of the oil film, and exceeds the theoretical oil film thickness $h_c$ (broken line or dashed line).

Figure 6:
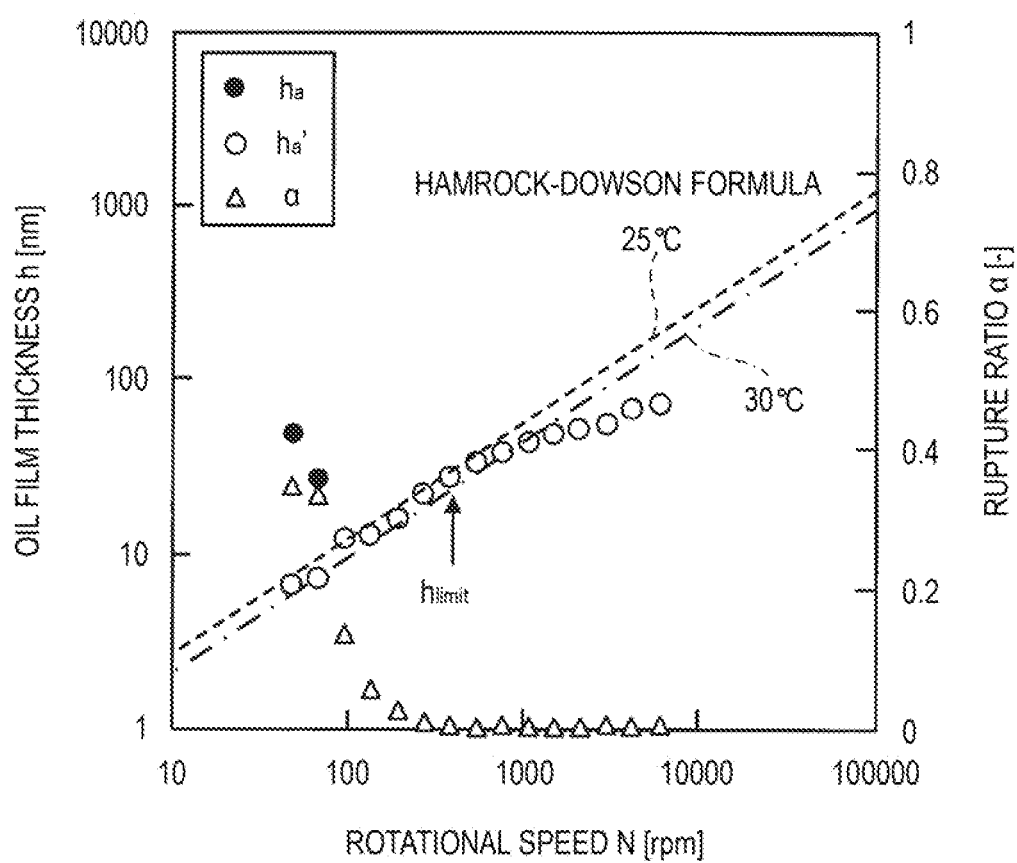
FIG. 6 is a graph in which the average oil film thickness after correction is superimposed on the graph of FIG. 5.

Therefore, the inventors placed importance on the above phenomenon, and measured the average oil film thickness $h_a'$ after correction by using Equation (23) derived from Equation (18) in consideration of the oil film thickness $h_{limit}$ and the rupture ratio α of the oil film at which metal contact starts to occur. FIG. 6 is a graph in which the average oil film thickness $h_a'$ after correction measured by using Equation (23) is superimposed on the graph of FIG. 5. $h_{limit}$ (the oil film thickness at which metal contact starts to occur) used in the measurement of Formula (23) was $h_a$ of the measurement point indicated by $h_{limit}$ in FIG. 5 or 6. In FIGS. 5 and 6, $h_{limit}$=27 nm at a rotation speed N=387 rpm.

From FIG. 6, it is understood that the average oil film thickness $h_a'$ after correction is approximately the same as the theoretical oil film thickness $h_c$ in the low rotational speed range of the rotational speed N. When the rotation speed is 100 rpm or more, the average oil film thickness $h_a$ and the average oil film thickness $h_a'$ after correction overlap each other, and only $h_a'$ in white circle is shown with emphasis on the visibility, and $h_a$ in black circle is not shown. From the above, it is estimated that at a predetermined rotational speed or higher, the oil film thickness increases and the rupture ratio α decreases, and therefore wear powder is not generated, and the event as shown in FIG. 3 does not occur.

Figure 7:
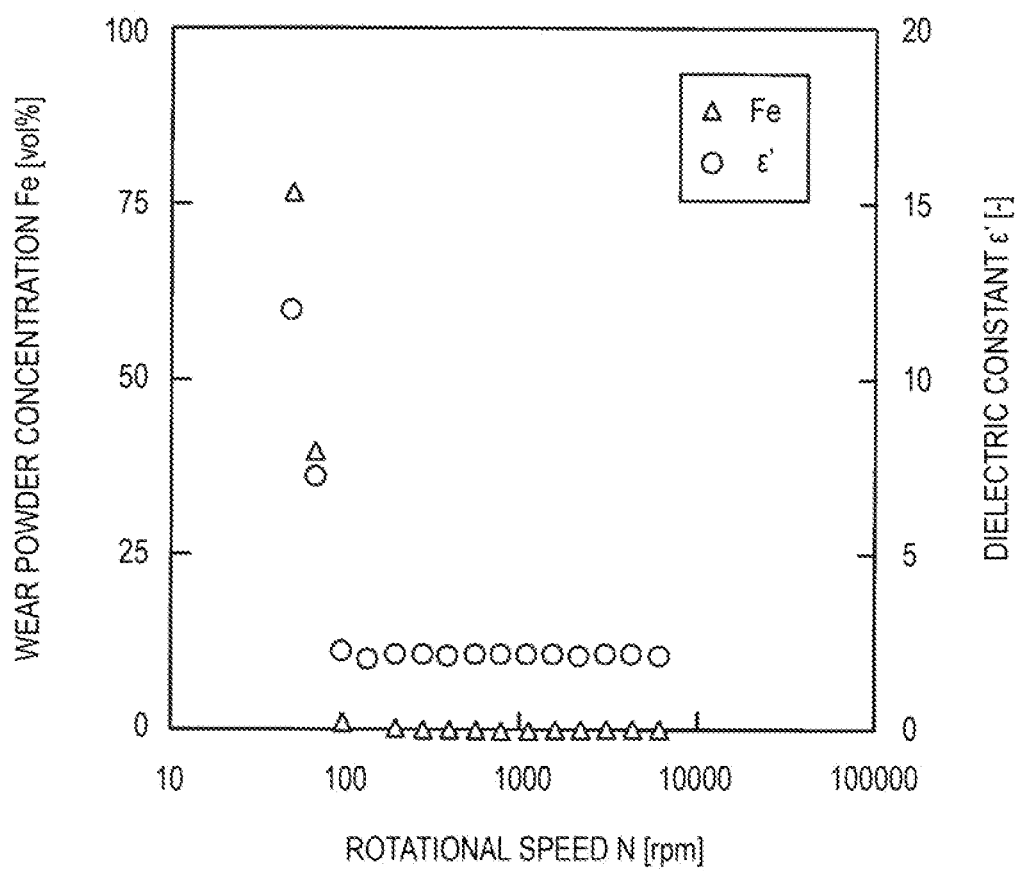
FIG. 7 is a graph of the wear powder concentration and the dielectric constant according to the rotational speed of the rotating shaft.

FIG. 7 is a graph showing the dielectric constant ε' of the lubricant calculated using Equation (25); FIG. 7 shows the wear powder concentration Fe of the lubricant. The wear powder concentration Fe was calculated from the measured ε' by using the relationship between the dielectric constant and the wear powder concentration shown in FIG. 3. Based on the wear powder concentration, the wear amount of the rolling apparatus 10, that is, the wear amount of at least one of between the outer ring (outer member) 1 and the rolling elements 5 or between the inner ring (inner member) 3 and the rolling elements 5 can be calculated. In particular, in the present embodiment, by using the electric circuit in FIGS. 2A and 2B, the measurement is performed using the current actually flowing in the vicinity of the contact area where the rolling elements 5 and the outer ring 1 or the inner ring 3 are in contact with each other, and the wear powder concentration and the wear amount in the vicinity of the contact area are calculated. Grasping the state in the vicinity of the contact area is very useful for grasping the actual operation state.

From FIG. 7, it was confirmed that the dielectric constant assumed in the low rotational speed range of the rotational speed N increased, and therefore, the wear powder concentration included in the lubricant was increased. Here, the wear powder concentration is terms of Li grease. As described above, according to the present embodiment, it can be observed from the measurement of the dielectric constant that some event, that is, an abnormality (which increases the dielectric constant) occurs in the contact area, without the necessity of calculating the wear powder concentration.

The present invention is not limited to the above embodiment, and modifications, improvements, and the like can be made as appropriate. Materials, shapes, sizes, numerical values, forms, numbers, arrangement positions, and the like of components in the above embodiment are arbitrary and not limited as long as the present invention can be achieved.

Although the embodiments are described above with reference to the drawings, it is needless to say that the present invention is not limited to such examples. It will be apparent to those skilled in the art that various changes and modifications may be conceived within the scope of the claims. It is also understood that the various changes and modifications belong to the technical scope of the present invention. Constituent elements in the embodiments described above may be combined freely within a range not departing from the spirit of the present invention.

The present application is based on Japanese Patent Application No. 2019-003990 filed on Jan. 15, 2019, the contents of which are incorporated herein by reference.

REFERENCE SIGNS LIST 1 outer ring (outer member)
3 inner ring (inner member)
5 rolling element
10 rolling apparatus (bearing apparatus)
12 rotary connector
14 motor
15 transmission member
16 rotating shaft
20 LCR meter
30 heat insulating container

The invention claimed is:

1. A method for diagnosing a rolling device including an outer member, an inner member, and a rolling element, the method for diagnosing the rolling device comprising:
   applying an AC voltage to an electric circuit including the outer member, the rolling element, and the inner member;
   measuring an impedance and a phase angle of the electric circuit when the AC voltage is applied; and
   deriving an oil film thickness and a rupture ratio of an oil film at least one of between the outer member and the rolling element and between the inner member and the rolling element based on the measured impedance and the measured phase angle; and
   measuring a dielectric constant of the lubricant using the oil film thickness and the rupture ratio of the oil film.

2. The method according to claim 1, further comprising:
   calculating a wear powder concentration of the lubricant from the measured dielectric constant.

3. The method according to claim 1, wherein the dielectric constant of the lubricant is calculated by the following equation $$\varepsilon' = \frac{\sin\theta'}{2\pi\omega|Z|\left(\frac{(1-\alpha)^2 a^2}{2h_a} + r\left(\ln\left(\frac{r(1-\alpha)}{h_a}\right) - 1\right)\right)},$$

wherein ε' is the dielectric constant of a lubricant, θ' is the phase angle, π is a circle rate, ω is an angular frequency of the AC voltage, Z is a complex impedance, α is the rupture ratio of the oil film, a is a Hertzian contact circle radius, $h_a$ is an average oil film thickness, and r is the radius of the rolling element.

4. The method according to claim 1, wherein the oil film thickness of the lubricant is calculated by the following equation $$h_1 = (1-\alpha) h_{limit},$$

wherein $h_1$ is the oil film thickness of the lubricant, α is a rupture ratio of the oil film, and $h_{limit}$ is the oil film thickness at which the metal contact starts to occur.

5. The method according to claim 1, wherein the oil film thickness of the lubricant is calculated by the following equation $$h_1 = (1-\alpha) \times 3\sqrt{R_{q1}^2 + R_{q2}^2},$$

wherein $h_1$ is the oil film thickness of a lubricant, α is the rupture ratio of the oil film of the lubricant, $R_{q1}$ is a surface roughness (mean square roughness) prescribed in JISB0601 (2013), and $R_{q2}$ is a surface roughness (mean square roughness) prescribed in JISB0601 (2013).

6. The method according to claim 1, wherein the oil film thickness of the lubricant is calculated by the following equation, $$h_1 = h_c/(1-\alpha),$$

wherein $h_1$ is the oil film thickness of the lubricant, $h_c$ is a theoretical oil film thickness, and α is the rupture ratio of the oil film.

7. The method according to claim 1, wherein the rupture ratio of the oil film of the lubricant is calculated by the following equation $$\alpha = |Z_0| \cos \theta'/|Z| \cos \theta_0,$$

wherein α is the rupture ratio of the oil film of the lubricant, $Z_0$ is a complex impedance in a stationary state, Z is a complex impedance, θ' is the phase angle, and $\theta_0$ is the phase angle in a stationary state.

* * * * *